United States Patent
Zhu et al.

(10) Patent No.: US 11,318,021 B2
(45) Date of Patent: May 3, 2022

(54) TOTAL HIP SURFACE REPLACEMENT IMPLANT

(71) Applicant: JIANGSU OKANI MEDICAL TECHNOLOGY CO., LTD, Taicang (CN)

(72) Inventors: Jack Zhu, Taicang (CN); Longwei Xu, Taicang (CN)

(73) Assignee: Jiangsu Okani Medical Technology Co., Ltd, Taicang (CN)

( * ) Notice: Subject to any disclaimer, the term of this patent is extended or adjusted under 35 U.S.C. 154(b) by 0 days.

(21) Appl. No.: 15/550,359

(22) PCT Filed: Sep. 25, 2015

(86) PCT No.: PCT/CN2015/000662
§ 371 (c)(1),
(2) Date: Aug. 10, 2017

(87) PCT Pub. No.: WO2016/127280
PCT Pub. Date: Aug. 18, 2016

(65) Prior Publication Data
US 2018/0028321 A1    Feb. 1, 2018

(30) Foreign Application Priority Data

Feb. 10, 2015    (CN) .......................... 201510070811.3

(51) Int. Cl.
*A61F 2/32*    (2006.01)
*A61L 27/16*    (2006.01)
(Continued)

(52) U.S. Cl.
CPC ................ *A61F 2/32* (2013.01); *A61L 27/04* (2013.01); *A61L 27/16* (2013.01); *A61L 27/18* (2013.01);
(Continued)

(58) Field of Classification Search
CPC ........ A61F 2/36; A61F 2/3603; A61F 2/3609; A61F 2/30724; A61F 2002/30245;
(Continued)

(56) References Cited

U.S. PATENT DOCUMENTS 2,622,592 A * 12/1952 Rosenstein ........... A61F 2/3603
                                                    623/23.11
2,650,588 A *  9/1953 Drew .................... A61F 2/3603
                                                    623/23.11
(Continued)

FOREIGN PATENT DOCUMENTS

CN    101904777 A    8/2010
CN    201899585 A    7/2011
(Continued)

OTHER PUBLICATIONS

Translated Written Opinion of the International Search Authority issued to PCT Application No. PCT/CN2015/000662 dated Jun. 30, 2017.
(Continued)

*Primary Examiner* — Alvin J Stewart
(74) *Attorney, Agent, or Firm* — Hackler Daghighian Martino & Novak (57) ABSTRACT

A total hip surface replacement implant, comprising a femur component and an acetabular cup component, wherein the femur component is in a half-spherical shell shape and is formed by polyether ether ketone (PEEK) or derivatives thereof; the shape of the acetabular cup component matches that of the femur component, and the acetabular cup component is tightly attached to an outer surface of the half-spherical shell of the femur component; the acetabular cup component is formed by ultrahigh molecular weight polyethylene; or the femur component can be formed by ultrahigh molecular weight polyethylene, and meanwhile the acetabular cup component is formed by polyether ether
(Continued)

ketone (PEEK) or derivatives thereof. The total hip surface replacement implant employs friction combination between organic polymers so as to reduce material toxicity against a living body; the rigidity of the organic polymers more matches that of a natural bone of a human body, thereby reducing implant wearing in a usage process; and by means of an optimization design of a positioning column on a femur condyle, the clinic problems of early neck-of-femur fracture and medium-and-long term bone resorption are avoided.

10 Claims, 4 Drawing Sheets

(51) Int. Cl.

| | | |
|---|---|---|
| *A61L 27/18* | (2006.01) | |
| *A61L 27/32* | (2006.01) | |
| *A61L 27/30* | (2006.01) | |
| *A61L 27/04* | (2006.01) | |
| *A61L 27/28* | (2006.01) | |
| *A61L 27/56* | (2006.01) | |
| A61F 2/30 | (2006.01) | |

(52) U.S. Cl.
CPC ............ *A61L 27/28* (2013.01); *A61L 27/306* (2013.01); *A61L 27/32* (2013.01); *A61L 27/56* (2013.01); *A61F 2002/3092* (2013.01); *A61L 2430/02* (2013.01)

(58) Field of Classification Search
CPC .......... A61F 2002/30649; A61F 2/3094; A61F 2002/30878; A61F 2002/30014; A61F 2/32; A61F 2/34; A61F 2002/30317
See application file for complete search history.

(56) References Cited

U.S. PATENT DOCUMENTS

| | | | | | |
|---|---|---|---|---|---|
| 2,679,245 | A | * | 5/1954 | Timmermans | A61F 2/3603 623/23.11 |
| 4,878,919 | A | * | 11/1989 | Pavlansky | A61F 2/30907 623/23.18 |
| 4,938,774 | A | * | 7/1990 | Tepic | A61F 2/3662 623/23.32 |
| 5,181,930 | A | * | 1/1993 | Dumbleton | A61L 27/443 623/23.34 |
| 5,549,702 | A | * | 8/1996 | Ries | A61F 2/3676 623/23.32 |
| 5,981,827 | A | * | 11/1999 | Devlin | C04B 41/85 623/23.51 |
| 6,096,084 | A | * | 8/2000 | Townley | A61F 2/3601 623/23.12 |
| 6,228,123 | B1 | * | 5/2001 | Dezzani | A61F 2/3662 623/23.32 |
| 6,258,126 | B1 | * | 7/2001 | Colleran | A61F 2/38 623/20.29 |
| 6,503,281 | B1 | * | 1/2003 | Mallory | A61B 17/8061 623/22.11 |
| 8,088,169 | B2 | * | 1/2012 | Dorr | A61F 2/30767 623/23.32 |
| 8,252,062 | B2 | * | 8/2012 | Bandoh | A61F 2/36 623/23.17 |
| 9,061,090 | B2 | * | 6/2015 | Bandoh | A61F 2/36 |
| 9,119,722 | B1 | * | 9/2015 | Kusuma | A61F 2/36 |
| 9,271,839 | B2 | * | 3/2016 | Armacost | A61F 2/3662 |
| 9,907,660 | B2 | * | 3/2018 | Wang | A61F 2/30767 |
| 10,213,314 | B2 | * | 2/2019 | Armacost | A61F 2/3662 |
| 2002/0065562 | A1 | * | 5/2002 | Storer | A61F 2/3603 623/22.46 |
| 2002/0072805 | A1 | * | 6/2002 | Sullivan | A61B 17/1668 623/23.42 |
| 2003/0014123 | A1 | * | 1/2003 | Copf | A61F 2/3603 623/23.14 |
| 2003/0074077 | A1 | * | 4/2003 | Taylor | A61F 2/34 623/22.26 |
| 2003/0163202 | A1 | * | 8/2003 | Lakin | A61F 2/32 623/22.15 |
| 2004/0193276 | A1 | * | 9/2004 | Maroney | A61B 5/1077 623/19.14 |
| 2005/0085915 | A1 | * | 4/2005 | Steinberg | A61B 17/1666 623/17.16 |
| 2005/0203633 | A1 | * | 9/2005 | Fernandes | A61F 2/32 623/22.11 |
| 2005/0256585 | A1 | * | 11/2005 | Park | A61F 2/3603 623/23.14 |
| 2005/0256586 | A1 | * | 11/2005 | Kraus | A61F 2/3603 623/23.16 |
| 2006/0085079 | A1 | * | 4/2006 | Carroll | A61F 2/32 623/22.15 |
| 2006/0184250 | A1 | * | 8/2006 | Bandoh | A61F 2/36 623/23.32 |
| 2006/0184251 | A1 | * | 8/2006 | Zhang | A61F 2/30767 623/23.56 |
| 2006/0190086 | A1 | * | 8/2006 | Clemow | A61F 2/38 623/20.15 |
| 2007/0208428 | A1 | * | 9/2007 | Tepic | A61F 2/34 623/22.32 |
| 2007/0227024 | A1 | * | 10/2007 | Beaule | A61F 2/4657 33/512 |
| 2007/0270975 | A1 | * | 11/2007 | Taylor | A61F 2/30771 623/23.5 |
| 2007/0276399 | A1 | * | 11/2007 | Medley | A61B 17/8802 606/92 |
| 2008/0004710 | A1 | * | 1/2008 | Ledger | A61F 2/3603 623/23.13 |
| 2008/0033577 | A1 | * | 2/2008 | Kohan | A61F 2/3603 623/32 |
| 2008/0167723 | A1 | * | 7/2008 | Acker | A61F 2/3662 623/22.4 |
| 2008/0200991 | A1 | * | 8/2008 | Collins | A61F 2/3603 623/23.12 |
| 2008/0215160 | A1 | * | 9/2008 | Grundei | A61F 2/32 623/22.39 |
| 2008/0262626 | A1 | * | 10/2008 | Raugel | A61F 2/30734 623/22.15 |
| 2009/0018666 | A1 | * | 1/2009 | Grundei | A61F 2/32 623/22.21 |
| 2009/0048681 | A1 | * | 2/2009 | Vlachos | A61F 2/3603 623/23.12 |
| 2009/0093887 | A1 | * | 4/2009 | Walter | A61F 2/30721 623/22.11 |
| 2009/0112315 | A1 | * | 4/2009 | Fang | A61L 27/56 623/11.11 |
| 2009/0149965 | A1 | * | 6/2009 | Quaid | A61B 17/1668 623/22.4 |
| 2009/0157191 | A1 | * | 6/2009 | Collins | A61F 2/3603 623/22.4 |
| 2009/0192610 | A1 | * | 7/2009 | Case | A61L 27/50 623/16.11 |
| 2009/0192620 | A1 | * | 7/2009 | Ebbitt | A61F 2/3603 623/18.11 |
| 2009/0209963 | A1 | * | 8/2009 | Jamali | A61B 17/1635 606/81 |
| 2009/0248170 | A1 | * | 10/2009 | Tuke | A61B 17/175 623/23.11 |
| 2009/0287311 | A1 | * | 11/2009 | Preuss | A61F 2/34 623/22.24 |
| 2009/0306788 | A1 | * | 12/2009 | Timoteo | A61B 17/15 623/23.14 |
| 2010/0049329 | A1 | * | 2/2010 | Vio | A61F 2/3603 623/23.12 |
| 2010/0076570 | A1 | * | 3/2010 | Band | A61F 2/30767 623/23.12 |
| 2010/0094430 | A1 | * | 4/2010 | Krumdieck | A61F 2/30767 623/23.5 |

(56) References Cited

U.S. PATENT DOCUMENTS

| | | | |
|---|---|---|---|
| 2010/0262144 A1* | 10/2010 | Kelman | A61F 2/34 606/62 |
| 2010/0262250 A1* | 10/2010 | Kellar | A61F 2/30767 623/18.11 |
| 2010/0298944 A1* | 11/2010 | Bishop | A61F 2/3603 623/18.11 |
| 2010/0298949 A1* | 11/2010 | McMinn | A61F 2/3601 623/23.36 |
| 2010/0305713 A1* | 12/2010 | Grundei | A61F 2/3603 623/23.12 |
| 2010/0312348 A1* | 12/2010 | Wang | A61F 2/38 623/18.11 |
| 2010/0312354 A1* | 12/2010 | Bandoh | A61F 2/3662 623/23.15 |
| 2011/0087333 A1* | 4/2011 | Kellar | A61F 2/32 623/20.35 |
| 2011/0153025 A1* | 6/2011 | McMinn | A61F 2/30771 623/20.32 |
| 2011/0202140 A1* | 8/2011 | Turner | A61F 2/36 623/22.4 |
| 2011/0264233 A1* | 10/2011 | Song | A61B 17/744 623/22.42 |
| 2012/0029650 A1* | 2/2012 | Bruce | A61F 2/3603 623/22.4 |
| 2012/0150315 A1* | 6/2012 | Forsell | A61F 2/32 623/23.13 |
| 2012/0165951 A1* | 6/2012 | Forsell | A61F 2/34 623/22.4 |
| 2012/0209396 A1* | 8/2012 | Myung | A61F 2/30 623/22.11 |
| 2012/0213911 A1* | 8/2012 | Bucciotti | B22F 5/10 427/2.26 |
| 2013/0060347 A1* | 3/2013 | McMinn | A61F 2/3603 623/23.23 |
| 2013/0261761 A1* | 10/2013 | Whitaker | A61F 2/3601 623/22.16 |
| 2013/0345827 A1* | 12/2013 | Wallick | A61F 2/28 623/23.58 |
| 2014/0180424 A1* | 6/2014 | Dickerson | A61F 2/3609 623/19.12 |
| 2014/0257512 A1* | 9/2014 | Liu | A61F 2/3603 623/23.14 |
| 2014/0303743 A1* | 10/2014 | Choudhury | A61F 2/32 623/22.24 |
| 2015/0025647 A1* | 1/2015 | Zhang | A61F 2/32 623/22.18 |
| 2015/0250597 A1* | 9/2015 | Lang | A61F 2/3609 623/22.12 |
| 2015/0335437 A1* | 11/2015 | Bruun Lauritzen | A61F 2/30756 623/23.12 |
| 2016/0113771 A1* | 4/2016 | McMinn | A61F 2/3603 623/23.11 |
| 2016/0228255 A1* | 8/2016 | Samuelson | A61F 2/3859 |
| 2017/0086980 A1* | 3/2017 | Suckow | A61F 2/34 |
| 2018/0000598 A1* | 1/2018 | Amis | A61F 2/3662 |
| 2018/0028718 A1* | 2/2018 | Zhu | A61F 2/3859 |
| 2018/0228616 A1* | 8/2018 | Piecuch | B22F 7/004 |
| 2018/0325695 A1* | 11/2018 | Wozencroft | A61F 2/4607 |
| 2019/0224367 A1* | 7/2019 | Kourtis | A61F 2/28 |
| 2021/0030550 A1* | 2/2021 | Ek | A61F 2/30749 |

FOREIGN PATENT DOCUMENTS

| | | |
|---|---|---|
| CN | 102276864 A | 12/2011 |
| CN | 204618485 U | 9/2015 |
| GB | 2139098 A | 7/1984 |
| GB | 2396561 A | 6/2004 |

OTHER PUBLICATIONS

Translated International Search Report issued to PCT Application No. PCT/CN2015/000662 dated Aug. 18, 2016.

* cited by examiner

TOTAL HIP SURFACE REPLACEMENT IMPLANT

TECHNICAL FIELD

The present disclosure relates to a medical rehabilitation instrument, and more particularly to a total hip replacement implant.

BACKGROUND

In recent years, the researchers have found that the friction surface between a new generation of high stability, high strength and high biocompatibility of polyether ether ketone (PEEK) polymer materials and the ultrahigh molecular weight polyethylene (UHMWPE) has higher wear resistance than that between CoCrMo and polyethylene (Wang AG, Zhang ZT, Lawrynowicz DE and Yau SS (2010) Orthopedic PAEK-on-polymer bearings, HOWMEDICA OSTEONICS CORP, IPC8 Class: AA61F230FI, USPC Class: 623 1811, Patent application number: 20100312348, 2010 Dec. 9; Singh, V, Ogden, C, Sitton, K and Sitton, K (2012) Wear evaluation of different polymeric materials for total disc replacement (TDR), Proceedings of the ASME/STLE International Joint Tribology Conference, Los Angeles, Calif., 2011, 35-37, 2012). This finding provides feasible experimental data for PEEK-to-polyethylene as a manual joint friction surface combination. Because polyether ether ketone and polyethylene have more matched rigidity with the natural bone of the human body, this combination may solve the problem of metal ion toxicity present in artificial joint replacement of CoCrMo-to-CoCrMo.

However, after researching, it has been found that the friction of the sliding surface of PEEK-to-polyethylene in terms of the amount of the wear (16.5±1.8 mm$^3$/million, Wang A G, Zhang Z T, Lawrynowicz DE and Yau S S (2010) ORTHOPEDIC PAEK-ON-POLYMER BEARINGS, HOWMEDICA OSTEONICS CORP, IPC8 Class: AA61F230FI, USPC Class: 623 1811, Patent application number: 20100312348, 2010 Dec. 9) of the ball-and-socket structure in the total hip replacement is not very ideal, we think this is due to the rigidity of the PEEK prosthesis femur component in the total hip replacement is not enough, resulting in instability of the rotation axis, making the friction surface of the ball-and-socket structure unstable, increasing the amount of the wear of the ball-socket structure surface. Thus, the application effect about the wear of the sliding surface of PEEK-to-polyethylene is not sufficiently ideal in the total hip replacement.

The total hip surface replacement ideally has many advantages over all hip replacement (Amstutz, H. C., Grigoris, P., and Dorey, F. J. Evolution and future of surface replacement of the hip. J. Orthop. Sci., 1998, 3, 169-186). Firstly, a large number of femoral bones are preserved in the surface replacement; secondly, the surface replacement adopts the femoral bone with the equivalent size of the natural bone of the human body, thereby the stability of the joint is greatly improved; finally, once there is a problem occurred in the surface replacement, the surface replacement can be overhauled through the traditional total hip replacement, thereby reducing the degree of removal for the natural bone of the patient.

Early in the thirties of last century, the total hip surface replacement has been applied to treatment of arthritis patients. Early studies have focused on Polymeric materials polytetrafluoroethylene (PTFE), trying the combination of the friction surface of PTFE (Charnley, J. Arthroplasty of the hip: a new operation. Lancet, 1961, 1, 1129-1132), but this was terminated due to excessive wear, resulting in poor tissue reaction and prosthesis destruction (Charnley, J. Tissue reactions to polytetrafluoroethylene (letter). Lancet, 1963, 2, 1379). Since it came into the second half of the last century, the wear combination of CoCrMo alloy-to-CoCrMo alloy has been widely used in the total hip replacement (August A C, Aldam C H, Pynsent P B. The McKee-Farrar hip arthroplasty. A long-term study. J Bone Joint Surg Br. 1986 August; 68(4): 520-7). Entering into the seventies of last century, as ultrahigh molecular weight polyethylene is successfully applied in the artificial hip replacement by Charnley, the total hip replacement of CoCrMo alloy-to-CoCrMo alloy was gradually eliminated, instead it is the friction surface combination of CoCrMo-to-ultrahigh molecular weight polyethylene (Wroblewski B M. Charnley low-friction arthroplasty. Review of the past, present status, and prospects for the future. Clin Orthop Relat Res. 1986 September; (210): 37-42). Since it came into the nineties of the last century, the friction combination of CoCrMo-to-CoCrMo has been also reapplied in surface replacement clinical by means of improvements in metallurgy and design (Sieber, H. P., Rieker, C. B., and Kottig, P. Analysis of 118 second generation metal-on-metal retrieved hip implants. J. Bone Jt Surg., 1999, 81B, 46-50; McMinn, D., Treacy, R., Lin, K., and Pynsent, P. Metal-on-metal surface replacement of the hip. Clin. Orthop., 1996, 329S, S89-S98). Since it came into the twenty-first century, CoCrMo-to-CoCrMo has been further applied in surface replacement (Grigoris P, Roberts P, Panousis K, Jin Z. Hip resurfacing arthroplasty: the evolution of contemporary designs. Proc Inst Mech Eng H. 2006 February; 220(2): 95-105. Review). However, due to the case that the wear of CoCrMo alloy and the adverse reactions to the human body caused by its ions increases, the friction combination of CoCrMo-to-CoCrMo was quickly withdrawn from clinical application, including the total hip replacement and the total hip surface replacement (Singh G, Meyer H, Ruetschi M, Chamaon K, Feuerstein B, Lohmann C H, Large-diameter metal-on-metal total hip arthroplasties: a page in orthopedic history, J Biomed Mater Res A. 2013 November; 101(11): 3320-6. doi: 10.1002/jbm.a.34619. Epub 2013 Mar. 25).

CoCrMo alloy-to-CoCrMo alloy has some defects in surface replacement, that is, in addition to the toxicity of the metal abrasive grains and the metal ions (Delaunay C, Petit I, Learmonth I D, Oger P, Vendittoli P A. Metal-on-metal bearings total hip arthroplasty: the cobalt and chromium ions release concern. Orthop Traumatol Surg Res. 2010 December; 96(8): 894-904. doi: 10.1016/j.otsr.2010.05.008. Epub 2010 Sep. 15), the rigidity of which is far higher than that of the natural bone of the human body, and due to the rigidity of the metal is higher during use, the stress is concentrated on the metal replacement implant, so that the bones around the implant are weakened, the implant cannot be combined with the bone, and the implant is prone to falling off and breaking in the later period, etc.

SUMMARY

In order to solve the above-mentioned problems and defects, the object of the present disclosure is to provide a total hip surface replacement implant. The total hip replacement implant can reduce the stress between the hip remaining bone and the implant, and reduce the wear of the implant.

In order to achieve the above object, the present disclosure employs the following technical solutions:

A total hip surface replacement implant, comprising a femur component and an acetabular cup member, wherein:

a shape of the femur component is hemispherical shell;

a shape of the acetabular cup component is matched with that of the femur component, and is tightly attached to an outer surface of the hemispherical shell of the femur component; and the femur component is formed of polyether ether ketone or derivatives thereof, the acetabular cup component is formed of ultrahigh molecular weight polyethylene; or the femur component is formed of ultrahigh molecular weight polyethylene, the acetabular cup component is formed of polyether ether ketone or derivatives thereof.

Further, the roughness Ra of the outer surface of the hemispherical shell of the femur component is less than 1.0 μm, and the roughness Ra of an inner surface of hemispherical shell of the femur component is greater than 0.1 μm.

Further, an inner central portion of the hemispherical shell of the femur component is provided with a solid positioning column.

Further, an inner central portion of the hemispherical shell of the femur component is provided with a hollow positioning column in which there is provided with a metal column core.

Further, an upper end of the metal column core is lower than a combined portion of the femur surface component with the positioning column.

Further, the inner surface of the hemispherical shell and an outer surface of the positioning column are coated with cementless materials.

Further, the inner surface of the hemispherical shell and an outer surface of the positioning column are provided with a layer of porous metal layer, the thickness of the porous metal layer is greater than 0.5 mm and the porosity is higher than 20%.

Further, the acetabular cup component is a highly cross-linked ultrahigh molecular weight polyethylene.

Further, a side of the acetabular cup component which is connected with a bone is coated with cementless materials.

Further, a side of the acetabular cup component which is connected with a bone is provided with a layer of porous metal layer, the thickness of the porous metal layer is less than 0.5 mm and the porosity is higher than 20%.

Due to the employment of the above technical solutions, the present disclosure has the following advantages compared with the prior art:

The total hip surface replacement implant of the present disclosure reduces the toxicity of the material to the organism due to the use of the friction combination of organic polymer-to-organic polymer, in addition, the organic polymer especially employs the combination of polymer material polyether ether ketone(PEEK)-to-ultrahigh molecular weight polyethylene (UHMWPE), the rigidity of which is more matched with the natural bone of the human body, achieving a certain buffering effect in motion, reducing the wear of the implant to ball-and-socket structure during use; due to the adding of a metal column core, the clinic problems resulting in early neck-of-femur fracture and medium-and-long term bone resorption are avoided.

LIST OF REFERENCE SIGNS

100 femur component, 110 hemispherical shell of femur component, 111 outer surface of hemispherical shell, 112 inner surface of hemispherical shell, 113 PEEK outer layer, 114 component combined with PEEK and metal foam, 115 metal barrier, 116 cementless materials, 120 positioning column, 121 outer surface of positioning column, 122 metal column, 200 acetabular cup component, 201 polymer layer, 202 component combined with polymer and metal foam, 203 metal barrier, 204 cementless materials.

DETAILED DESCRIPTION

In order to make the objects, technical solutions and advantages of the present disclosure more clearly understood, the present disclosure will be described in further detail with reference to the accompanying drawings and embodiments below. It should be understood that the specific embodiments described herein are only used to explain the present disclosure and are not intended to limit the present disclosure.

Figure 1:
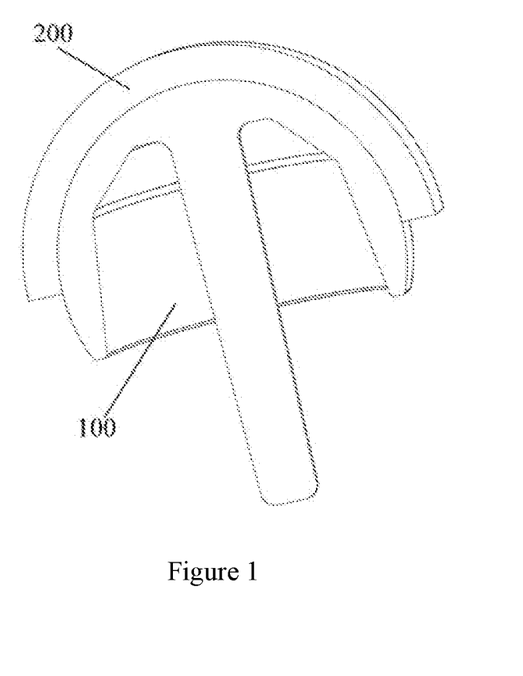
FIG. 1 is a schematic view of one embodiment of a novel total hip surface replacement implant of the present disclosure.
Figure 2:
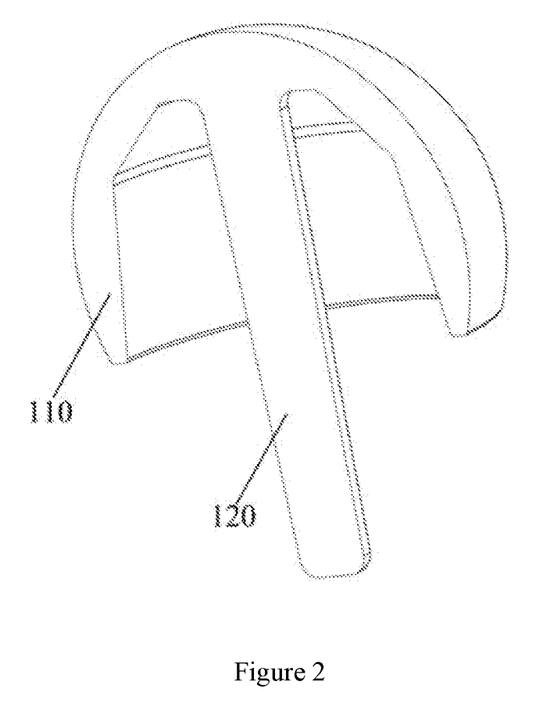
FIG. 2 is a schematic view of one embodiment of a femur component of a novel total hip surface replacement implant of the present disclosure.

As shown in FIG. 1 and FIG. 2, the novel total hip surface replacement implant of the present disclosure comprises a femur component 100 and an acetabular cup component 200, wherein: the femur component 100 comprises a hemispherical shell 110 and is formed of polyether ether ketone (PEEK) or derivatives thereof, the PEEK can comprise a developing additive, the shape of the acetabular cup component 200 is matched with that of the hemispherical shell 110 of the femoral component 100 and is tightly attached to an outer surface 111 of the hemispherical shell 110 of the femoral component 100, the acetabular cup component 200 is formed of ultrahigh molecular weight polyethylene.

In a preferred embodiment, the femur component 100 is formed of ultrahigh molecular weight polyethylene, while the acetabular cup component 200 is formed of polyether ether ketone (PEEK) or derivatives thereof; the PEEK can comprise a developing additive.

In a preferred embodiment, as shown in FIG. 2, a solid positioning column 120 with a circular or conical section is arranged at the inner central portion of the hemispherical shell 110 of the femur component 100, and is used to fix the femur component on a bone of the human body.

Figure 3:
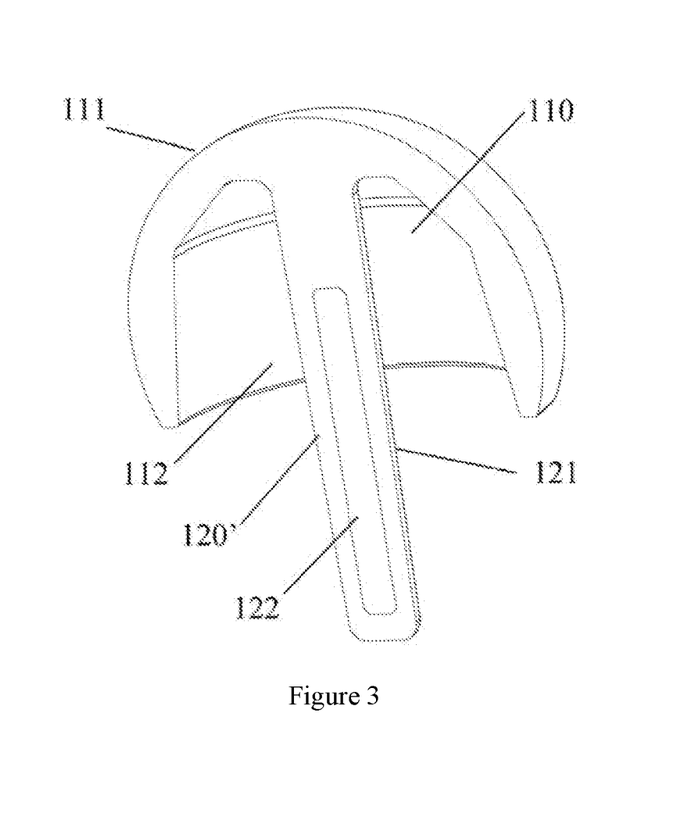
FIG. 3 is a schematic view of one embodiment of a femur component of a novel total hip surface replacement implant of the present disclosure.

In a preferred embodiment, as shown in FIG. 3, a hollow positioning column 120' with a circular or conical section is arranged at the inner central portion of the hemispherical shell 110 of the femoral component 100, and a metal column core which is matched with the shape and the size of the hollow positioning column 120' is embedded into the hollow interior of the hollow positioning column 120', an upper end of the metal column core is lower than the combined portion of the hemisphere shell 110 of the femur with the positioning column 120'. In the initial stage of implantation of the implant, a partial gap is also existed between the hemispherical shell 110 and the bone, while the rigidity of the organic polymer material is not enough to stabilize the structure, the instability of axis will result in the friction surface of the ball-and-socket structure being easily stressed in different directions, quickening the failure of the material. Setting the metal pillar core can play the role in reinforcing, but the position of the metal column core has a greater influence on the service life of the material. When the top of the metal column core is higher than the combined position of the femur hemisphere shell 110 with the positioning column 120', due to the elasticity modulus of the metal being high, the stress subjected by the femur component is mostly concentrated on the metal column core, the stress of the ball socket is lower, the growth of bones in the ball socket is weakened, the bone cannot be engaged with the implant, the support of the implant parts depends on the metal column core for a long time, which is easy to cause fractures. As a result, the upper end of the metal column core should be lower than the combined portion of the positioning column with the hemispherical shell, so that the mid-long-term bone growth of the region can be increased, and the bone absorption of the region is avoided to result in the positioning column becoming an independent stressed portion, thereby finally causing the fracture.

On the other hand, the roughness Ra of the outer surface 111 of the hemispherical shell 110 is less than 1.0 µm, preferably, Ra is less than 0.1 µm, the better the surface smoothness is, and the lower the friction between the PEEK outer layer and the acetabular cup component 200 in use is, the smaller the wear of the component is, the roughness Ra of an inner surface 112 of the hemispherical shell 110 is greater than 0.1 µm, preferably, Ra is greater than 1 µm. The inner surface 112 is in contact with the human bone, and the roughness of which can affect the binding force between the implant and the bone.

Figure 4:
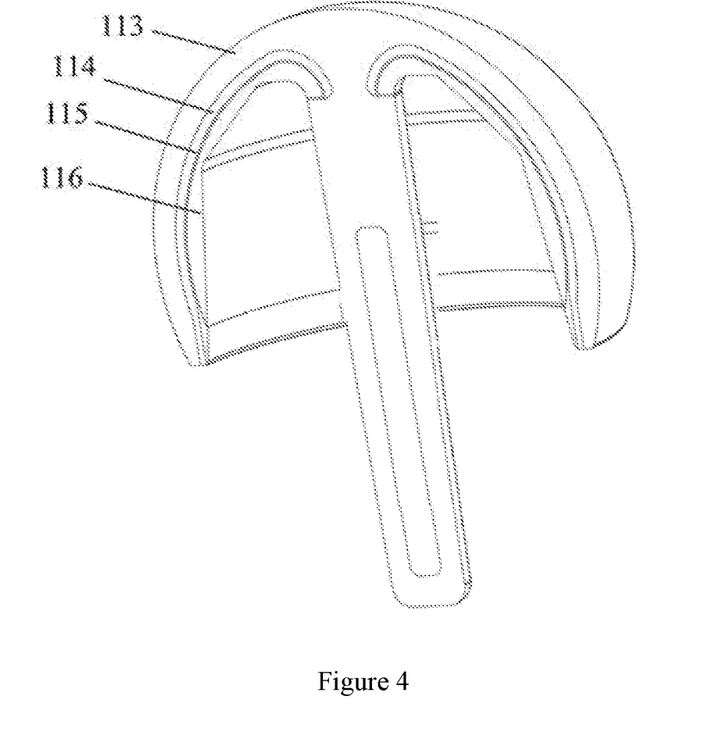
FIG. 4 is a schematic view of one embodiment of a femur component of a novel total hip surface replacement implant of the present disclosure.

In a preferred embodiment, as shown in FIG. 2 and FIG. 4, the outer surface 111 of the hemispherical shell 110 and an outer surface 121 of the positioning column 120, 120' are coated with cementless materials 116, which are mainly a biological immobilized coating, including but not limited to hydroxyapatite (HA), titanium or titanium alloy coating, tantalum or tantalum alloy, zirconium-niobium alloy coating and the like, which is used to facilitate the combination between the implant and the bone, thereby playing a role in fixing.

In a preferred embodiment, as shown in FIG. 4, a porous metal layer, including but not limited to metal foam, is arranged on the inner surface 112 of the hemispherical shell 110, the outer layer of the hemispherical shell 110 is PEEK 113, a metal barrier 115 is arranged inside the PEEK outer layer 113 and has the effect on supporting the whole shell and also has a developing effect, in order to achieve a solid combination between the PEEK outer layer 113 and the metal barrier 115, a component 114 that combines PEEK with metal foam is arranged between them. In addition, the outer surface 121 of the positioning column is also provided with a porous metal layer, the thicknesses of the porous metal layer of the hemispherical shell 110 and the positioning column 120, 120' are greater than 0.5 mm and the porosity is higher than 20%, the bone can be inserted into the metal gap, the implant can be firmly combined with the bone through such structure.

In a preferred embodiment, the porous metal layer employed in the present disclosure is formed by laser or electron beam 3D printing, the porous metal layer and the femur component are combined by mechanical extrusion embedding or injection molding.

In a preferred embodiment, the acetabular cup component is a highly cross-linked ultrahigh molecular weight polyethylene.

Figure 5:
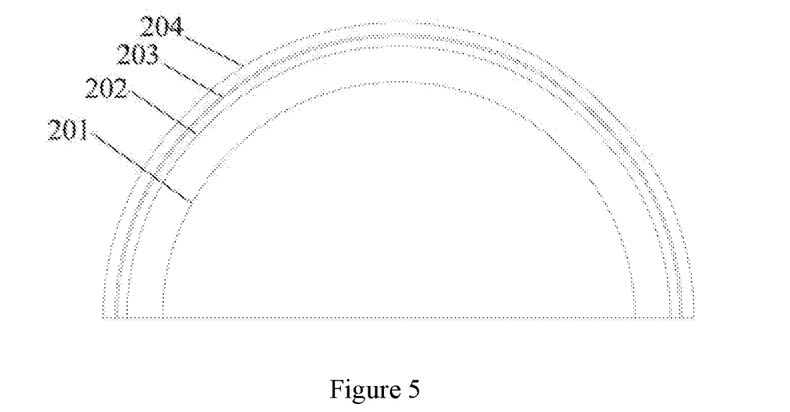
FIG. 5 is a schematic illustration of one embodiment of an acetabular cup member of a novel total hip surface replacement implant of the present disclosure.

In a preferred embodiment, as shown in FIG. 5, the inner surface of the acetabular cup component 200 is a polymer layer 201 with high smoothness, the outer layer of the acetabular cup component 200 is a metal barrier 203, a component 202 that combines polymer with metal foam is arranged between the polymer layer 201 and the metal barrier 203, the outer layer of the metal barrier is also provided with cementless materials 204 including but not to limited to hydroxyapatite (HA), titanium or titanium alloy coating, tantalum or tantalum alloy, zirconium-niobium alloy coating, etc, which is used to facilitate the combination between the implant and the bone, thereby playing a role in fixing.

In a preferred embodiment, a side of the acetabular cup component 200 which is connected with the bone is provided with a layer of porous metal layer, the thickness of the porous metal layer is less than 0.5 mm and the porosity is higher than 20%, the bone can be inserted into the metal gap, so that the implant can be firmly combined with the bone through such structure.

The above descriptions are only preferred embodiments of the present disclosure and are not intended to limit the implementation scope of the present disclosure; modifications or equivalent substitutions of the present disclosure should be covered in the protective scope of the claims of the present disclosure without departing from the spirit and scope of the disclosure.

The invention claimed is:

1. A total hip surface replacement implant, comprising a femur component and an acetabular cup component, wherein:
   the femur component comprises a hemispherical composite shell and a hollow positioning column, the hemispherical composite shell comprises an outer layer, a porous metal layer, and a metal barrier layer, the outer layer extends inwards at an inner central portion of the hemispherical composite shell, the hemispherical composite shell couples to the hollow positioning column at the inner central portion;
   the acetabular cup component is adapted to receive the femur component, the acetabular cup component having an inner surface rotatably coupled to the outer surface of the hemispherical composite shell of the femur component;
   the outer surface of the hemispherical composite shell and the hollow positioning column are formed of polyether ether ketone (PEEK) or derivatives thereof and the acetabular cup component is formed of ultrahigh molecular weight polyethylene (UHMWPE);
   the inner surface of the acetabular cup component and the outer surface of the hemispherical shell of the femur component forming a UHMWPE-to-PEEK juncture; and
   the hollow positioning column having an interior cavity with a metal column core.

2. The total hip surface replacement implant of claim 1, characterized in that, the roughness Ra of the outer surface of the hemispherical shell of the femur component is less than 1.0 µm, and the roughness Ra of an inner surface of the hemispherical shell of the femur component is greater than 0.1 µm.

3. The total hip surface replacement implant of claim 1, characterized in that, the inner surface of the hemispherical shell and an outer surface of the positioning column are coated with cementless materials.

4. The total hip surface replacement implant of claim 1, characterized in that, the inner surface of the hemispherical shell and an outer surface of the positioning column are provided with a layer of porous metal layer, the thickness of the porous metal layer is greater than 0.5 mm and the porosity is higher than 20%.

5. The total hip surface replacement implant of claim 1, wherein an upper end of the metal column core is lower than a combined portion of the femur component with the positioning column.

6. The total hip surface replacement implant of claim 1, wherein the inner surface of the hemispherical shell and an outer surface of the positioning column are coated with cementless materials.

7. The total hip surface replacement implant of claim 1, wherein the inner surface of the hemispherical shell and an outer surface of the positioning column are provided with a layer of porous metal layer, the thickness of the porous metal layer is greater than 0.5 mm and the porosity is higher than 20%.

8. The total hip surface replacement implant of claim 1, characterized in that, the acetabular cup component is a highly cross-linked ultrahigh molecular weight polyethylene.

9. The total hip surface replacement implant of claim 1, characterized in that, a side of the acetabular cup component which is connected with a bone is coated with cementless materials.

10. The total hip surface replacement implant of claim 1, a side of the acetabular cup component which is connected with a bone is provided with a layer of porous metal layer, the thickness of the porous metal layer is less than 0.5 mm and the porosity is higher than 20%.

* * * * *